United States Patent
Chang

(10) Patent No.: US 11,925,739 B2
(45) Date of Patent: Mar. 12, 2024

(54) ARTIFICIAL KIDNEY

(71) Applicant: Seagate Technology LLC, Fremont, CA (US)

(72) Inventor: Thomas Y. Chang, Menlo Park, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 576 days.

(21) Appl. No.: 17/076,610

(22) Filed: Oct. 21, 2020

(65) Prior Publication Data

US 2021/0121619 A1    Apr. 29, 2021

Related U.S. Application Data

(60) Provisional application No. 62/984,886, filed on Mar. 4, 2020, provisional application No. 62/925,077, filed on Oct. 23, 2019.

(51) Int. Cl.
| | |
|---|---|
| *A61M 1/34* | (2006.01) |
| *A61M 1/16* | (2006.01) |
| *A61M 1/30* | (2006.01) |
| *B01D 61/28* | (2006.01) |
| *B01D 63/08* | (2006.01) |

(52) U.S. Cl.
CPC .......... *A61M 1/34* (2013.01); *A61M 1/1631* (2014.02); *A61M 1/1633* (2014.02); *A61M 1/1654* (2013.01); *A61M 1/1678* (2013.01); *A61M 1/301* (2014.02); *A61M 1/3417* (2014.02); *B01D 61/28* (2013.01); *B01D 63/082* (2013.01); *B01D 63/084* (2013.01); *B01D 63/085* (2013.01); *B01D 63/087* (2013.01); *A61M 2205/04* (2013.01); *A61M 2205/75* (2013.01); *A61M 2206/10* (2013.01); *A61M 2206/16* (2013.01); *A61M 2209/088* (2013.01); *A61M 2210/1082* (2013.01); *B01D 2313/205* (2022.08)

(58) Field of Classification Search
CPC .............. A61M 1/1654; A61M 1/1631; A61M 1/1633; A61M 1/1678; A61M 1/301; A61M 1/34; A61M 1/3417; A61M 2205/04; A61M 2205/75; A61M 2206/10; A61M 2206/16; A61M 2209/088; A61M 2210/1082; B01D 61/28; B01D 63/082; B01D 63/084; B01D 63/085; B01D 63/087; B01D 2313/20
See application file for complete search history.

(56) References Cited

U.S. PATENT DOCUMENTS

| | | | |
|---|---|---|---|
| 5,092,886 | A | 3/1992 | Dobos-Hardy |
| 10,159,777 | B2 | 12/2018 | Reggiani et al. |
| 10,172,991 | B2 | 1/2019 | Gerber et al. |
| 2018/0344913 | A1 | 12/2018 | Nguyen et al. |

OTHER PUBLICATIONS

Office Action from corresponding Chinese patent application 202011148648.5, dated Sep. 23, 2023.

*Primary Examiner* — John Kim
(74) *Attorney, Agent, or Firm* — HOLZER PATEL DRENNAN

(57) ABSTRACT

An implantable or wearable kidney enclosure that is cylindrical, ovoid, or otherwise non-angular e.g., not rectangular or cuboid), having a circular or oval hemofilter that provides a blood flow pattern from an internal, central artery source radially outwards. Due to the efficient flow of the circular filter design, the enclosure can be made in a cylindrical low profile shape, resulting in a compact enclosure highly suitable for implantable and wearable dialysis applications.

15 Claims, 10 Drawing Sheets

ARTIFICIAL KIDNEY

CROSS-REFERENCE

This application claims priority to U.S. provisional application 62/925,077 filed Oct. 23, 2019 titled "Artificial Kidney" and to U.S. provisional application 62/984,886 filed Mar. 4, 2020 titled "Artificial Kidney," the entire disclosures of which are incorporated herein by reference for all purposes.

BACKGROUND

When a person's kidneys no longer function properly, kidney transplants and dialysis are the current solution to the ailing kidneys, which are no longer able to filter toxins from the body. However, dialysis—which filters out some (but not all) toxins from the bloodstream that would normally be eliminated by the kidneys—must be performed on a daily basis if done at home via peritoneal dialysis. Three visits per week are needed to a clinic if performed via hemodialysis.

Work is ongoing to develop an implantable artificial kidney that can closely replicate the functions of real kidneys. If successful, it could help eliminate the need for dialysis.

An artificial kidney is a surgically implanted, freestanding bioartificial kidney that performs much of the filtration, balancing, and other biological functions done by of the natural kidney. Powered by the body's own blood pressure, an artificial kidney does not require the external tubes or tethers associated with wearable artificial kidneys.

As indicated above, work is still ongoing.

SUMMARY

This disclosure is directed to an implantable or wearable, low profile artificial kidney enclosure having a radial blood flow pattern. The enclosure is cylindrical, ovoid, or otherwise non-angular (e.g., not rectangular, cuboid, rhomboid, etc.). In some implementations, all external edges are rounded, leaving no angular exposed edges. Within the enclosure is an annular, e.g., circular or oval, filter plate.

This disclosure provides, in one particular implementation, an artificial kidney, having an annular hemofilter having a circular or oval shape, the hemofilter having a central axis, and an enclosure having a cross-sectional shape corresponding to the hemofilter taken orthogonal to the central axis. The enclosure further has an interior volume for receiving the annular hemofilter therein, an inlet proximate the central axis fluidly connected to the interior volume to receive a flow of blood therein, an outlet fluidly connected to the interior volume to receive a flow of blood therefrom, and a second outlet fluidly connected to the interior volume to receive a flow of toxins therefrom. The inlet is fluidly connected to a first chamber in the enclosure and the outlet is fluidly connected to a second chamber in the enclosure, the first and second chambers separated by the annular hemofilter.

The disclosure also provides, in another particular implementation, an artificial kidney having an annular hemofilter having a circular or oval shape, the annular hemofilter having an inner diameter and an outer diameter, and an enclosure having a shape corresponding to the hemofilter, the enclosure having an interior volume for receiving the hemofilter therein. The artificial kidney has a radial blood flow path across the annular hemofilter from the inner diameter to the outer diameter.

This disclosure further provides, in an implementation, a method of filtering blood by providing an artificial kidney having an annular hemofilter having a circular or oval shape, the annular hemofilter having an inner diameter and an outer diameter, and flowing blood radially across the annular hemofilter from the inner diameter to the outer diameter. The method can include flowing blood radially across a second annular hemofilter from its outer diameter to its inner diameter.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

DETAILED DESCRIPTION

Both externally wearable and implantable (internal) artificial kidney enclosure designs thus far have been rectilinear or square in shape, to house rectangular hemofilters. However, the boxy enclosures with corners (whether the corners are actually sharp or radiused) are not desirable for implantable devices, as they must be carefully placed during implantation and can be uncomfortable or irritating once implanted. For the rectangular filters housed within rectilinear enclosures, the flow of blood is from one end of the device to the other end, passing over the hemofilter. The blood has a uniform flow over the surface of the filter from a single arterial inlet source.

Figure 1:
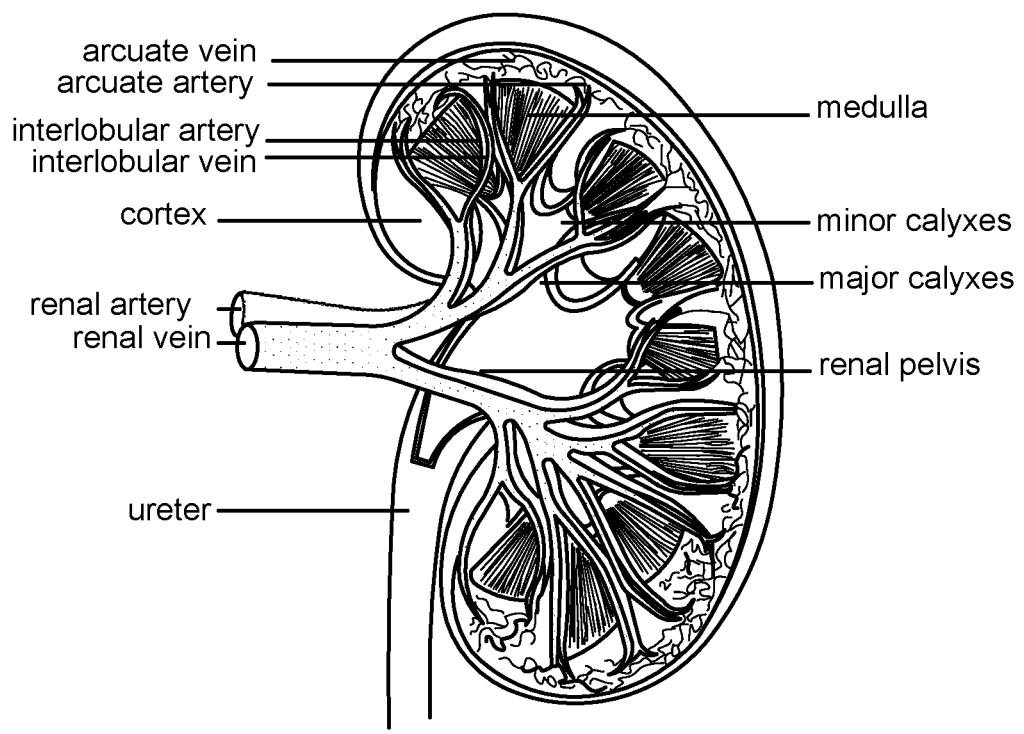
FIG. 1 is a diagram of a human kidney.

However, the blood flow pattern in a natural kidney has blood entering from a single artery which then fans out over a distribution of capillaries across a larger area. FIG. 1 illustrates a natural, human kidney, showing the single artery entering the kidney and then dividing into a fan-like array of capillaries. A circular or oval plate filter, housed within a cylindrical, ovoid, or otherwise non-angular enclosure, according to this disclosure, provides a blood flow pattern similar to a real kidney, across the hemofilter plate from a central artery source radiating out to the outer diameter of the filter.

Thus, this disclosure is directed to an implantable or wearable, low profile artificial kidney enclosure having a radial blood flow pattern. The enclosure is cylindrical, ovoid, or otherwise non-angular (e.g., not rectangular or cuboid). In some implementations, all external edges are rounded or radiused, leaving no angular exposed edges. Internal spaces that sandwich the filter plates have intricate blood flow control fins or tubing to provide additional blood flow control and blood distribution across the circular or otherwise non-angular filter plate.

The circular or oval hemofilter provides a blood flow pattern from an internal, central artery source radially outwards. The area around the filter plate can have intricate blood flow control fins or tubing to provide additional blood flow control and blood distribution across the circular filter. Control of the pressure profile (pressure difference or differential) between the blood side and the dialysate side of the hemofilter ensures the pressure difference does not cause damage (e.g., irreversible fractures or deformation) to the filter plate.

Due to the efficient flow of a circular filter design, the enclosure can be made in a cylindrical shape and low profile resulting in a compact enclosure highly suitable for implantable and wearable dialysis applications.

The design provides a compatible smooth exterior shape and small low profile compact design for an implantable kidney application. The radial blood flow pattern closely mimics the flow pattern in an actual kidney, where blow flows in from a single artery source in a small area to a broad area and uniformly distributes the blood across the filter.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples provided below.

A medical drawing of a normal, human kidney is shown in FIG. 1. The various enclosures and hemofilters described herein are used in place of such a kidney, when the kidney is not available or is no longer functioning properly. As seen in FIG. 1, single renal artery enters the kidney and then divides into a fan-like array of capillaries. The blood returns to a single renal vein.

Figure 2:
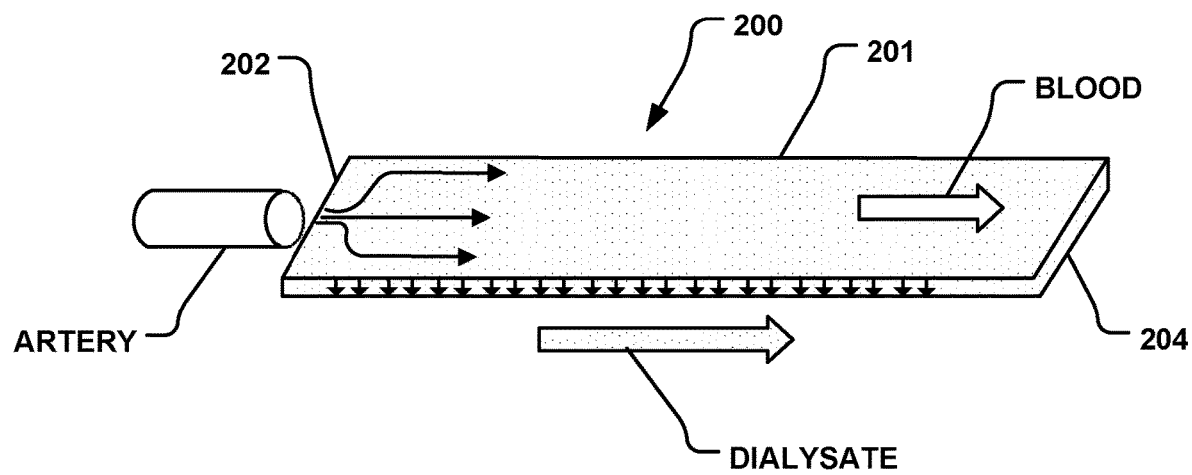
FIG. 2 is a schematic diagram of a conventional rectangular kidney hemofilter.

FIG. 2 schematically illustrates blood flow in a conventional rectangular hemofilter 200 having a filter plate 201. Blood enters at a first end 202 and flows relatively linearly the length of the filter to a second, opposite end 204. Dialysate, separated from the blood by the filter plate 201, flows essentially concurrently with the blood. Toxins from the blood flow through the filter plate 201 to the dialysate, flowing from the top through to the bottom of the filter plate 201, in this rendering.

Figure 3:
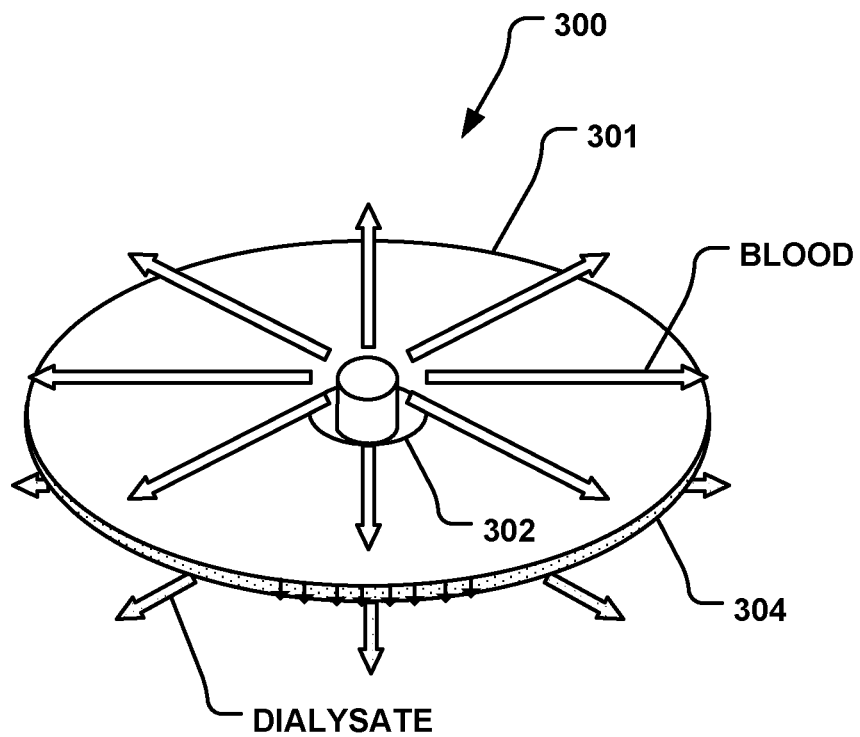
FIG. 3 is a schematic diagram of a circular kidney hemofilter.

FIG. 3 schematically illustrates a circular hemofilter 300 having a filter plate 301 and a blood flow pattern for the filter 300 from a central hole 302 radially outward to the periphery 304. Due to the central hole 302, the circular filter plate 301 is annular. This flow of blood from the center hole 302 or a center region out toward the outer periphery 304 of the filter plate 301 more closely mimics the flow pattern of a natural kidney shown in FIG. 1. Similar to the conventional hemofilter of FIG. 2, dialysate, separated from the blood by the filter plate 301, flows essentially concurrently with the blood, from the center region to the periphery. Toxins from the blood flow through the filter plate 301 to the dialysate, flowing from the top through to the bottom of the filter plate 301, in this rendering.

Figure 4A:
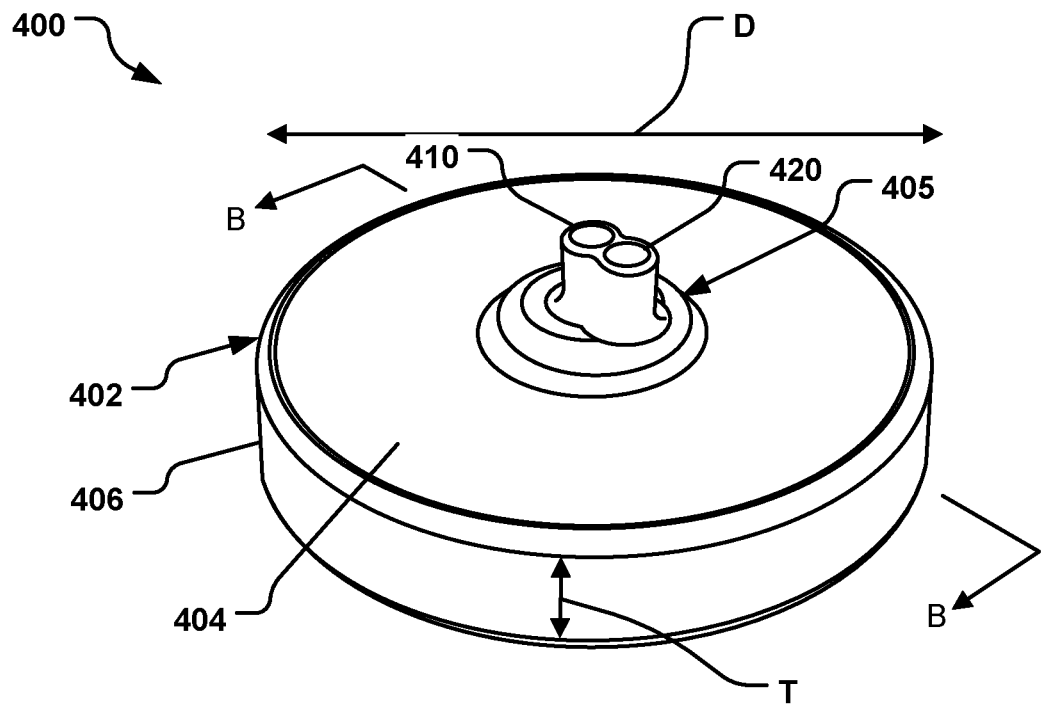
FIG. 4A is a perspective view of an artificial kidney low profile filter.
Figure 5:
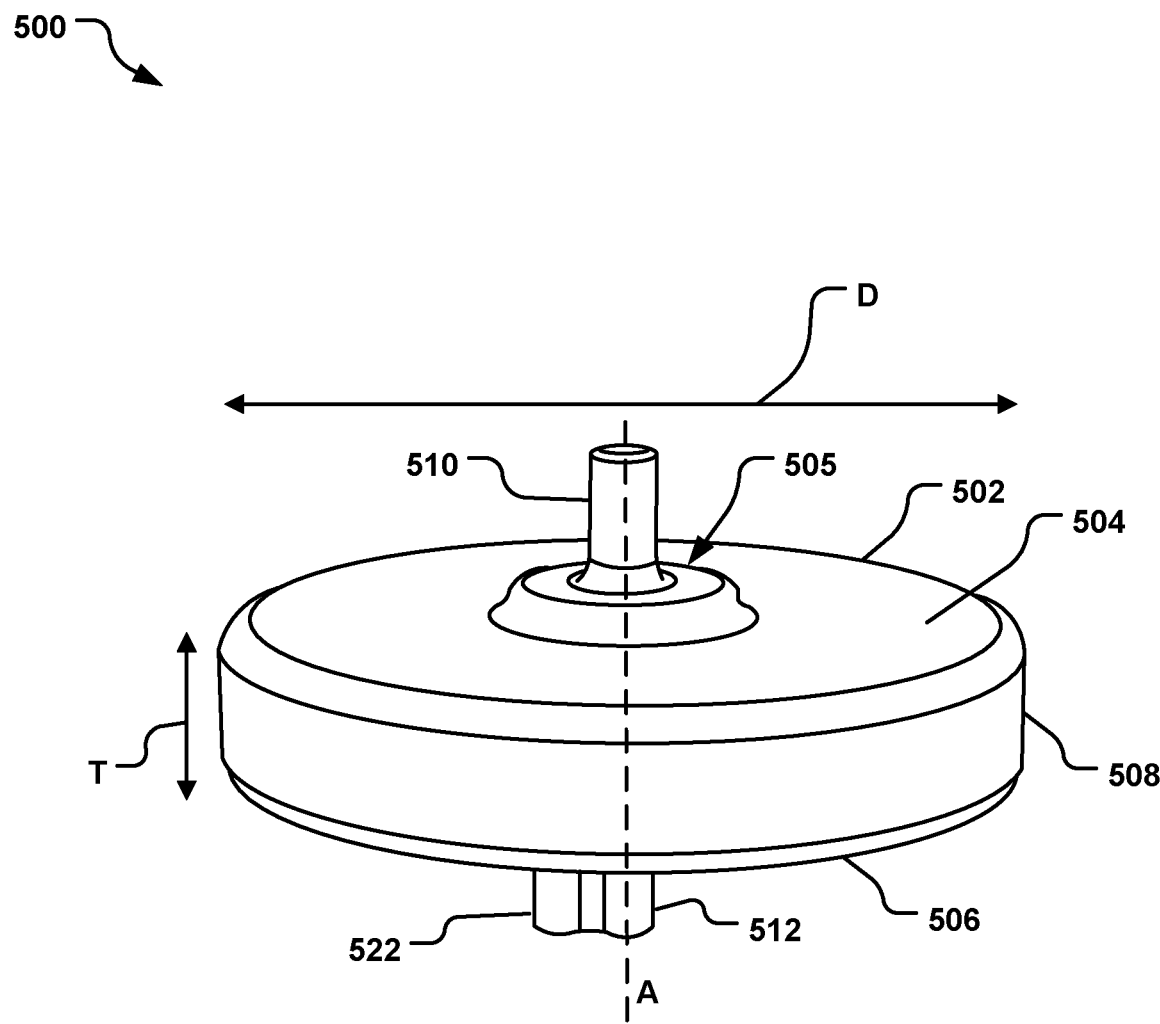
FIG. 5 is a perspective view of another artificial kidney low profile filter.

A circular hemofilter, such as filter 300 of FIG. 3, is used with a cylindrical enclosure, an example of which is shown in FIG. 4A and another example in FIG. 5, which are perspective views of generally cylindrical, low profile artificial kidney enclosures. In both implementations, it is seen that all outer or exposed edges are rounded. In some implementations, including these, the cylindrical enclosure has a low profile (and, could even be referred to as a disk or disc). A "low profile" refers to the thickness "T" dimension being significantly less than the diameter "D" of the enclosure as shown in FIG. 4A and in FIG. 5.

Turning specifically to FIG. 4A, a filter assembly 400 has an external enclosure 402 having a generally planar top surface 404, an opposite bottom surface (not seen) parallel to the top surface 404, and a periphery wall 406. The enclosure 402 has a thickness T that is the height of the wall 406. Positioned within the interior volume of the enclosure 402 is at least one filter or filter plate, having a shape corresponding to the shape of the enclosure, in this implementation, circular or annular.

Within a center region 405 of the top surface 404 of the enclosure 402 is a first inlet 410 and a second inlet 420. In this implementation, the first inlet 410 is blood (artery) input and the second inlet 420 is input for the dialysate (cleaning fluid).

Figure 4B:
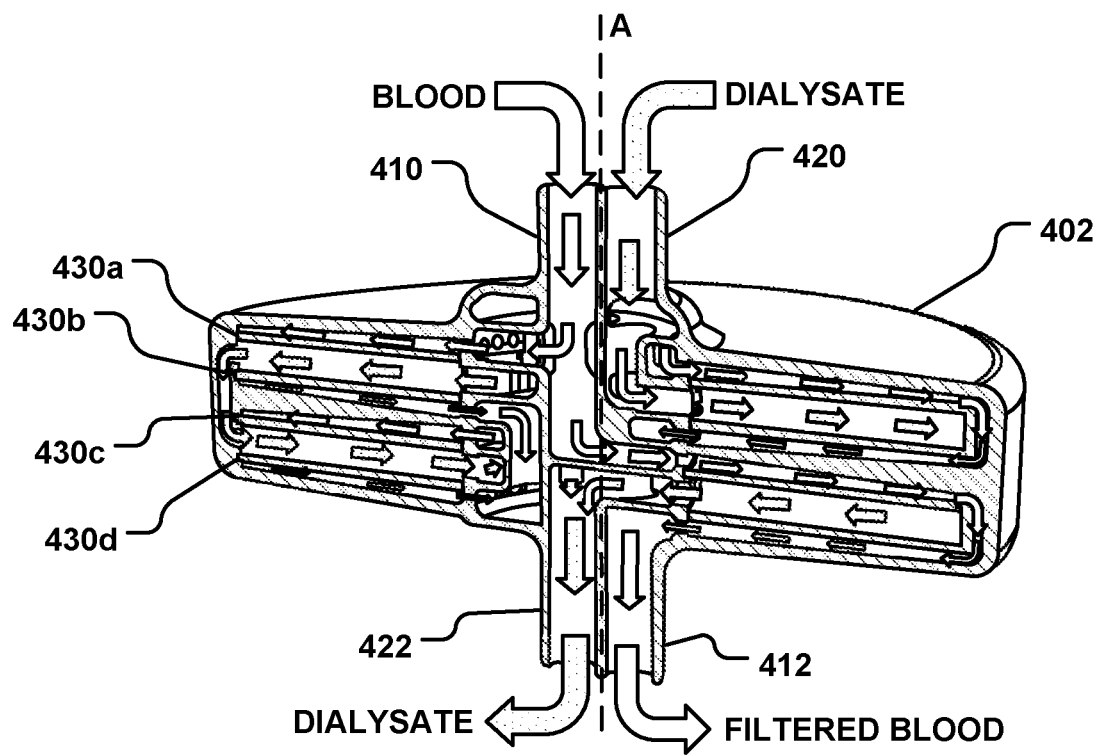
FIG. 4B is a cross-sectional view of the filter of FIG. 4A.

FIG. 4B shows the blood flow and dialysate flow within the filter assembly 400; it is noted that the entire internal structure (e.g., passages) of the interior of the enclosure 402 is not seen. The enclosure 402 has multiple annular filter plates 430 therein, shown as plates 430*a*, 430*b*, 430*c*, 430*d*. Dirty blood enters the enclosure 402 via the first inlet 410, which is positioned essentially at the center of the filter plates 430, and flows radially across a first side of the first filter plate 430*a*. Dialysate enters the enclosure 402 via the second, essentially centrally positioned, inlet 420, and flow radially below the first filter plate 430*a*, on the side opposite of the blood. Toxins in the blood pass through the filter plate 430 into the dialysate. Both the blood and dialysate circulate within the enclosure between the various plates 430 and eventually exit via a first outlet 412 as cleaned or filtered blood and via a second outlet 422 as dialysate carrying toxins. From the first outlet 412, the blood is returned to the pulmonary system and, from the second outlet 422, the dialysate is sent to a bioreactor or the like.

In FIG. 4B it is readily seen that the inlets 410, 420 and the outlets 412, 422 are positioned proximate a central axis A through the filter assembly 400, the enclosure 402, and the filter plates 430.

Turning to FIG. 5, a filter assembly 500 has an external enclosure 502 having a generally planar top surface 504, an opposite bottom surface 506 parallel to the top surface 504, and a periphery wall 508. The enclosure 502 has a thickness T that is the height of the wall 508. Positioned within the interior volume of the enclosure 502 is at least one filter or filter plate, having a circular or annular shape. Within a center region 505 of the top surface 504 of the enclosure 502 is an inlet 510 to receive blood (e.g., from an artery). Within a center region (not seen) of the bottom surface 506 is a first outlet 512 and a second outlet 522.

The inputted blood circulates within the enclosure 502 across the various filter plates in a radially outward and inward manner between the plates and eventually exits via a first outlet 512 as cleaned or filtered blood. As no dialysate was inputted to the filter assembly 500, plasma containing toxins and other waste exits via the second outlet 522, the plasma and toxins having been separated from the blood by the filter plates. From the first outlet 512, the blood is returned to the pulmonary system and, from the second outlet 522, the fluid is sent to a bioreactor or the like.

In FIG. 4B it is readily seen that the inlet 510 and the outlet 512 for the blood are positioned proximate a central axis A through the filter assembly 500 and the enclosure 502 and are similarly located on the top surface 504 in relation to the bottom surface 506 (e.g., they are aligned). The second outlet 522 for the waste is not aligned, as there is no corresponding inlet.

Various other flow configurations and configurations with multiple sets of plates that can be utilized.

Figure 6:
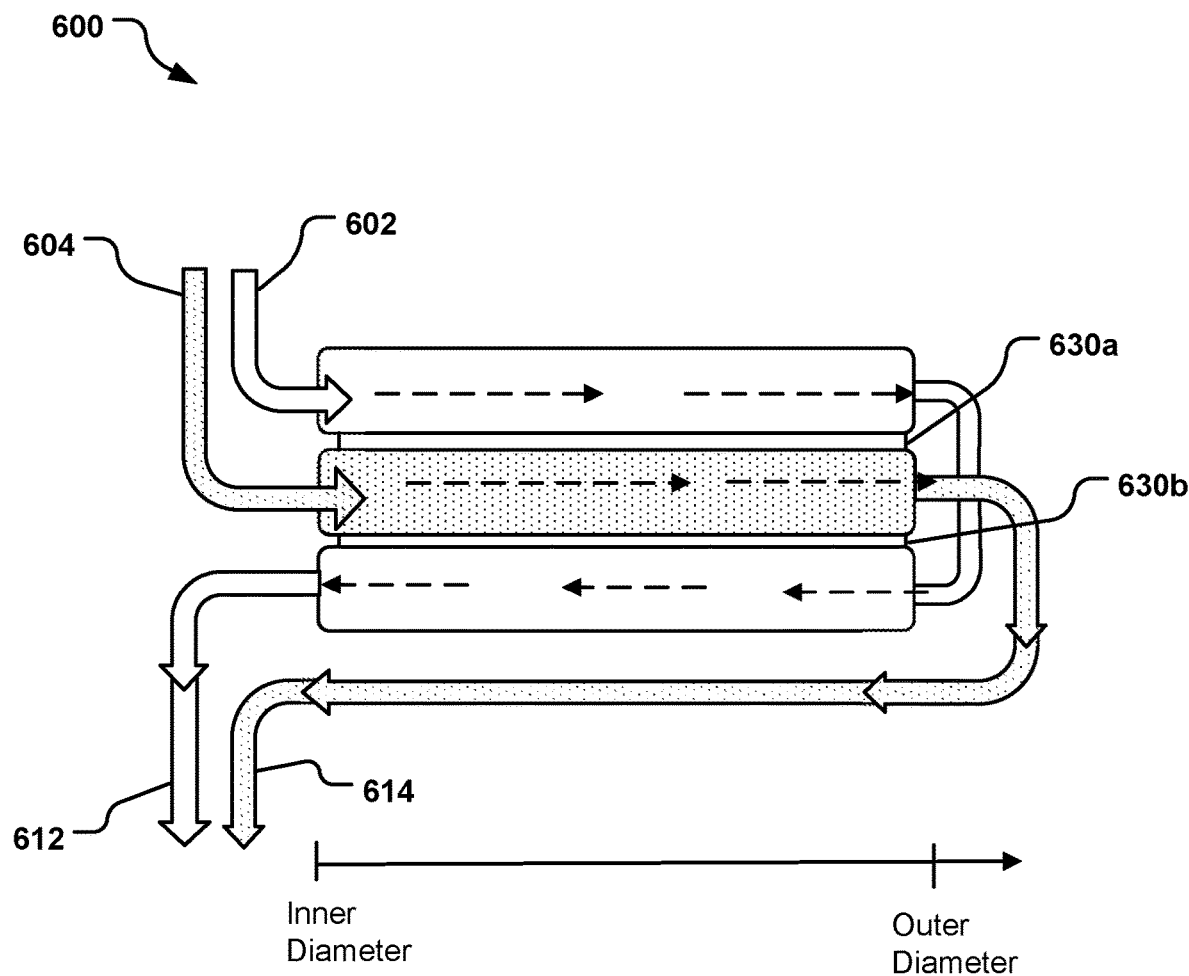
FIG. 6 is a schematic cross-sectional diagram of an example kidney filter.

An example is shown in FIG. 6, which is a schematic cross-sectional view of blood and dialysate flow over a pair of hemofilters. In this configuration, blood and clean dialysate comes into the enclosure at the inner diameter of the annular plate filter. First, the blood passes over the top filter in the upper chamber and toxins pass through the top filter plate into the clean dialysate. The blood flow continues to the outer diameter zone and passes back into the lower chamber where the filtering function continues through the lower filter plate as the blood flows from the outer diameter zone to the inner zone. Note that the reverse flow will perform the same filtering function and is independent of flow direction or any combination of flow direction for the blood and dialysate.

Specifically, an enclosure of a filter assembly 600 has a first inlet 602 for receipt of dirty blood and a second inlet 604 for receipt of dialysate, and a first outlet 612 for exit of cleaned or filtered blood and a second outlet 614 for exit of dialysate carrying toxins. The inlets 602, 604 and outlets 612, 614 are within the center of a stack of annular filter plates 630, in this implementation, filter plates 630a, 630b. It is noted that only half of the annular filter plates 630 are shown, identified with the axis at the bottom of the figure which indicates the inner diameter of the filter plates 630 and the outer diameter.

Dirty blood enters the enclosure via the first inlet 602 and flows radially across a first side of the first filter plate 630a from proximate the inner diameter to the outer diameter. Dialysate enters the enclosure via the second inlet 604, and flow radially below the first filter plate 630a, on the side opposite of the blood. Toxins in the blood pass through the filter plate 630a into the dialysate. Both the blood and dialysate circulate within the enclosure between the various plates 630, removing toxins from the blood and transferring to the dialysate; particularly, the blood flows radially out on a first surface of the filter plate 630a and then radially in on a second surface of the filter plate 603b, whereas the dialysate flows radially out between the second surface of the filter plate 630a and the first surface of the filter plate 630b.

Figure 7:
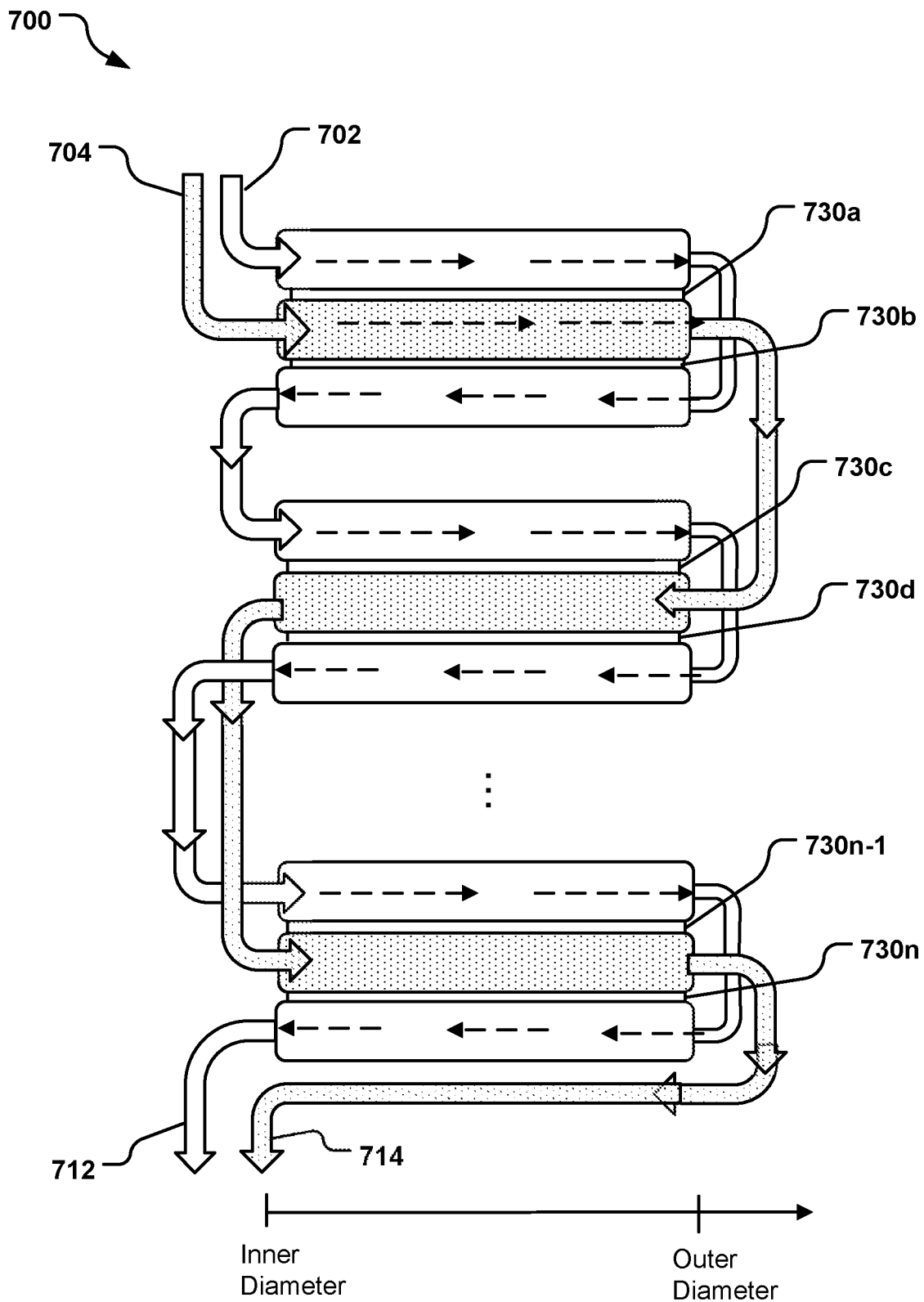
FIG. 7 is a schematic cross-sectional diagram of an example of multiple kidney filter units.

Another example is shown in FIG. 7, which is a schematic cross-sectional view of blood and dialysate flow over multiple filter unit pairs connected in a parallel configuration, where parallel blood flow refers to the input blood being connected directly to each filter unit.

Specifically; an enclosure of a filter assembly 700 has a first inlet 702 for receipt of dirty blood and a second inlet 704 for receipt of dialysate, and a first outlet 712 for exit of cleaned or filtered blood and a second outlet 714 for exit of dialysate carrying toxins. The inlets 702, 704 and the outlets 712, 714 are within the center of a stack of annular filter plates 730, in this implementation, filter plates 730a, 730b, 730c, 730d, ... 730n-1, 730n. It is noted that only half of the annular filter plates 730 are shown, identified with the axis at the bottom of the figure which indicates the inner diameter of the annular filter plates 730 and the outer diameter.

Dirty blood enters the enclosure via the first inlet 702 after which it splits; a first portion flows radially across a first side of the first filter plate 730a of the first pair from proximate the inner diameter to the outer diameter; a second portion flows radially across a first side of the first filter plate 730c of the second pair, and a nth portion flows radially across a first side of the first filter plate 730n-1 of the nth pair. The blood returns radially to the center of the annular filter plates 730; the first portion flows radially inward across a second side of the second filter plate 730b of the first pair, the second portion flows radially inward across a second side of the second filter plate 730d of the second pair, and the nth portion flows radially inward across a second side of the second filter plate 730n of the nth pair.

Dialysate enters the enclosure via the second inlet 704 after which it splits; a first portion flows radially outward between the first pair of filter plates 730a, 730b, a second portion flows radially outward between the second pair of filter plates 730c, 730d, and an nth portion flows radially outward between the nth pair of filter plates 730n-1, 730n.

As with the previous deigns, both the blood and dialysate circulate within the enclosure between the various plates 730, transferring toxins from the blood to the dialysate.

Figure 8:
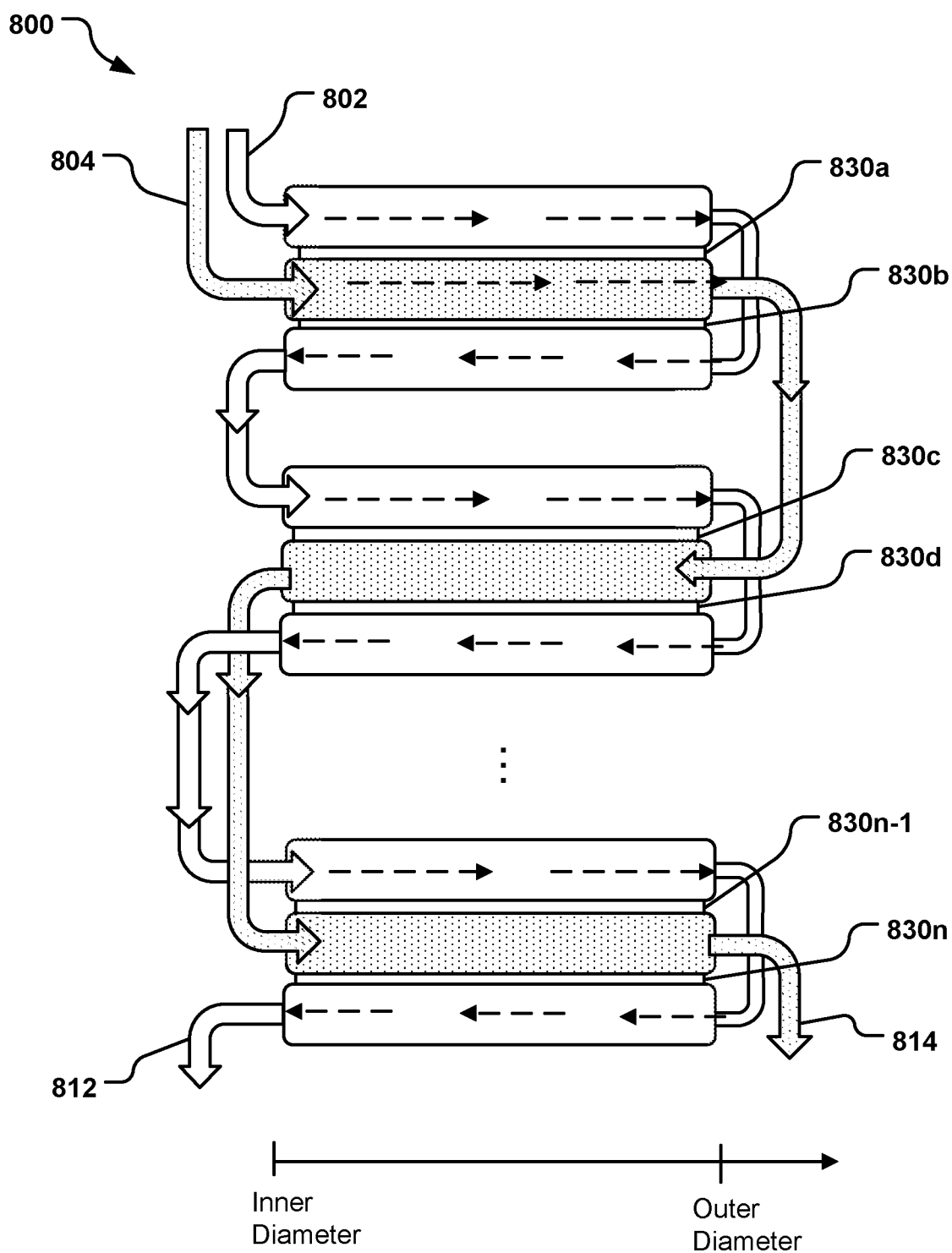
FIG. 8 is a schematic cross-sectional diagram of another example of multiple kidney filter units.

Another example is shown in FIG. 8, which is a schematic cross-sectional view of blood and dialysate flow for multiple filter units connected in a series flow configuration for both the blood flow from the artery and for the dialysate flow. In this series configuration, each filter pair is daisy-chained and the blood passes through the first pair, then through the second pair, etc., until the "n" pair.

Specifically, an enclosure of a filter assembly 800 has a first inlet 802 for receipt of dirty blood and a second inlet 804 for receipt of dialysate, and a first outlet 812 for exit of cleaned or filtered blood and a second outlet 814 for exit of dialysate carrying toxins. In this example, the inlets 802, 804 and the outlet 812 are within the center of a stack of annular filter plates 830 (in this implementation, filter plates 830a, 830b, 830c, 830d, ... 830n-1, 830n) and the outlet 814 for the dialysate is at the outer diameter of the filter plates 830. In this example, the outlet 814 is an annular outlet, extending around the periphery of the enclosure, whereas in other implementations, a series of channels or baffles may be used to direct the dirty dialysate to a single outlet, e.g., one centrally located or one proximate the periphery.

It is noted that, again, only half of the annular filter plates 830 are shown, identified with the axis at the bottom of the figure which indicates the inner diameter of the annular filter plates 830 and the outer diameter.

Dirty blood enters the enclosure via the first inlet 802 and flows radially across a first side of the first filter plate 830a of the first pair from proximate the inner diameter to the outer diameter and then returns flowing radially inward across a second side of the second filter plate 830b of the first pair. From the first pair, the blood flows radially across a first side of the first filter plate 830c of the second pair from proximate the inner diameter to the outer diameter and then returns flowing radially inward across a second side of the second filter plate 830d of the second pair. This flow continues until the blood flows radially across a first side of the first filter plate 830n−1 of the nth pair from proximate the inner diameter to the outer diameter and then returns flowing radially inward across a second side of the second filter plate 830n of the nth pair.

Dialysate enters the enclosure via the second inlet 804 and flows radially outward between the first pair of filter plates 830a, 830b, returns with a radially inward flow between the second pair of filter plates 830c, 830d, etc., and finally flows between the nth pair of filter plates 830n−1, 830n.

As with the previous deigns, both the blood and dialysate circulate within the enclosure between the various plates 830, removing toxins from the blood and transferring the toxins to the dialysate.

Although FIG. 7 illustrates all parallel flow and FIG. 8 illustrates all series flow, any combination of series and parallel blood and dialysate flow pattern can be utilized. The series flow pattern is easier to implement when daisy chaining multiple filter units together. However, the fluid (e.g., blood) pressure will be greater in the first filter unit that receives the initial blood input, and decrease in the higher order filter units; this may require increased mechanical strength requirements to support the higher mechanical pressure associated with the high operating pressure of the series design. The parallel flow configuration has the advantage of equal blood and dialysate operating pressure for each of the filter units. However, a parallel configuration requires a more complex enclosure design to accommodate multiple filter units.

Figure 9A:
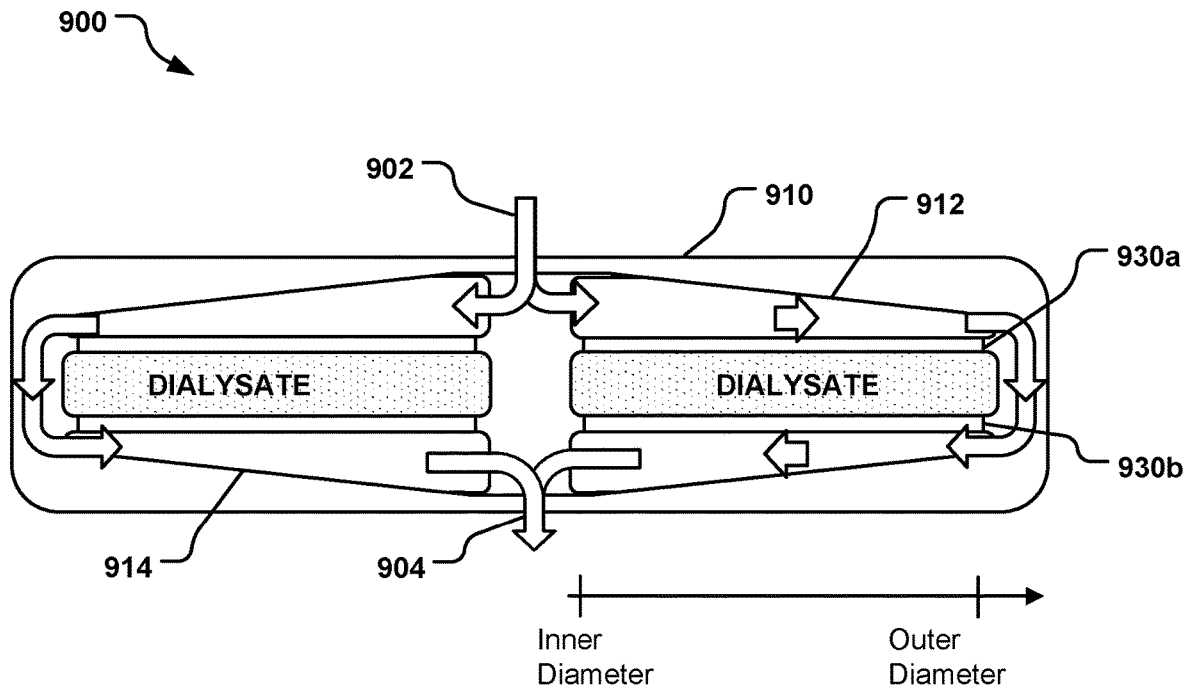
FIG. 9A is a schematic cross-sectional diagram of an example kidney filter.
Figure 9B:
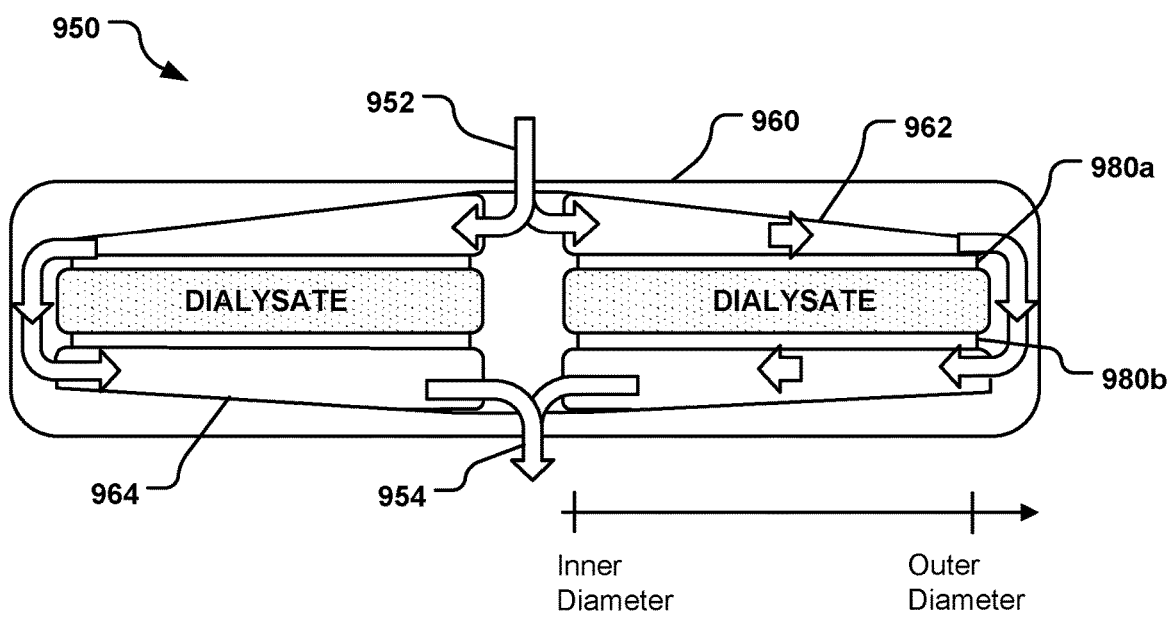
FIG. 9B is a schematic cross-sectional diagram of an alternate example kidney filter.

FIGS. 9A and 9B show two alternate enclosure shapes, both tapered from the center to the periphery, thus providing internal chambers for blood flow that decrease in volume as the distance from the center (inner diameter) increases. Although both FIG. 9A and FIG. 9B show enclosures having two filter plates (one pair) therein, these tapered shapes may be used for larger scale implementations.

FIG. 9A shows a cross-sectional view of a filter assembly 900 having one filter unit or pair, annular filter plates 930a, 930b, in an enclosure 910 having an upper chamber 912 and a lower chamber 914. The enclosure 910 has a blood inlet 902 and a blood outlet 904. Dirty blood enters the enclosure 910 via the inlet 902 and flows radially across a first side of the first filter plate 930a from proximate the inner diameter to the outer diameter and then returns flowing radially inward across a second side of the second filter plate 930b. The dialysate inlet, outlet, and flow direction are not shown in FIG. 9A for clarity, but described above, dialysate flow between the filter plates 930.

In FIG. 9A, as seen in the cross-section view, the upper chamber 912 and the lower chamber 914 are tapered such that the cross sectional area normal to the blood flow direction is roughly constant from the inner diameter to the outer diameter; this provides a roughly uniform blood pressure across the surface of the filter plate 930. A design that provides uniform pressure across the filter plates 930 simplifies the filter mechanical design to resist fractures. For example, the filter plates 930 can have uniform thickness and support spacing.

FIG. 9B shows a cross-sectional view of a filter assembly 950 also having one filter unit or pair, annular filter plates 980a, 980b, in an enclosure 960 having an upper chamber 962 and a lower chamber 964. The enclosure 960 has a blood inlet 952 and a blood outlet 954. Dirty blood enters the enclosure 960 via the inlet 952 and flows radially across a first side of the first filter plate 980a from proximate the inner diameter to the outer diameter and then returns flowing radially inward across a second side of the second filter plate 980b. The dialysate inlet, outlet, and flow direction are not shown in FIG. 9B for clarity, but described above, dialysate flow between the filter plates 980.

In FIG. 9B, as seen in the cross-section view, the upper chamber 962 and the lower chamber 964 are both tapered but they are asymmetric, unlike the chambers 912, 914 of FIG. 9A which are symmetric.

In FIG. 9B, the overall cross-section area of the lower chamber 964 is increased by a constant value with respect to the upper chamber 962 to maintain roughly similar pressure in the upper and lower chambers 962, 964 and between the surfaces of the filter plates 980. This asymmetric cross-sectional area to achieve equal pressure can be used in regions where there is series blood or dialysate flow. Even in a parallel configuration, a single filter pair has a serial path between the upper and lower chambers in the enclosure.

Thus, FIGS. 9A and 9B provide enclosure examples that provide uniform pressure across the plate filter surfaces and between the filter plates of a pair by having roughly uniform cross-sectional area normal to the flow of blood and dialysate.

A simple linear taper shape from the inner diameter to the outer diameter (or periphery) of the filter plates can be used to roughly maintain constant pressure across the surface. Other shape profiles, e.g., quadratic, exponential, etc., can be used to maintain a constant pressure profile, such as shown in FIG. TO.

Figure 10:
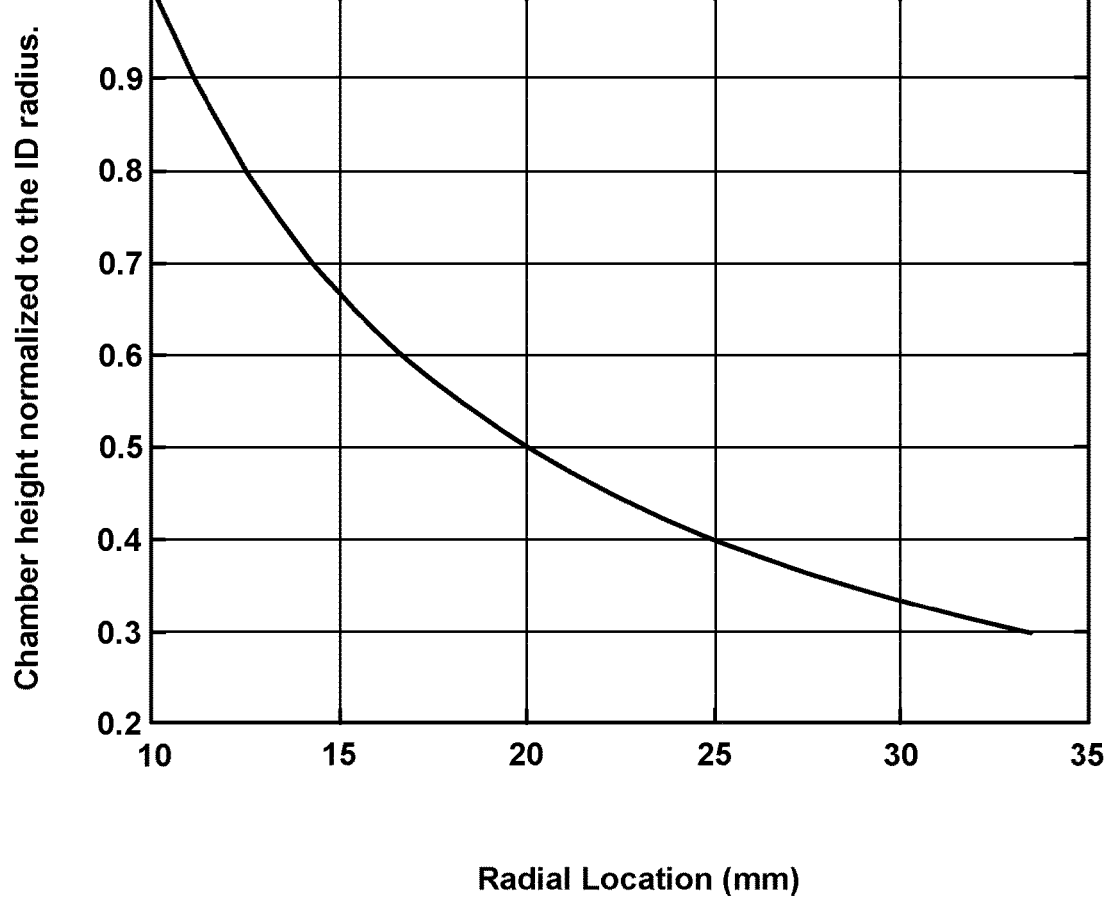
FIG. 10 is a graphical representation of a filter chamber profile.

FIG. 10, as graph 1000, shows a chamber height profile as related to the radius of a hemofilter plate (e.g., from the inner diameter to the outer diameter of the filter plate). In this particular example shown in FIG. 10, the inner radius is 10 mm, and outer radius is 33.5 mm. The y-axis represents the chamber height (h) and the x-axis represents the distance from the center of the filter plate. The graph 1000 shows a non-linear profile shape that follows the following equation to maintain constant flow cross sectional area: $h = R1/R$, where $R$ is the radial location on the filter and $R1$ is the inner radius of the filter.

In summary, described herein is an implantable or wearable kidney enclosure that is cylindrical, ovoid, or otherwise non-angular not rectangular or cuboid), configured to receive an annular circular or annular oval hemofilter. The annular filter has a blood flow pattern from an internal, central artery source radially outwards. Multiple filters, generally as pairs, may be present in the enclosure, configured in parallel or in series.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. An artificial kidney comprising:
   an annular hemofilter having a circular or oval shape, the hemofilter having a central axis; and
   an enclosure having a cross-sectional shape corresponding to the hemofilter taken orthogonal to the central axis, the enclosure further having:
       an interior volume for receiving the annular hemofilter therein,
       an inlet proximate the central axis fluidly connected to the interior volume to receive a flow of blood therein;
       an outlet proximate the central axis and fluidly connected to the interior volume to receive a flow of blood therefrom; and
       a second outlet fluidly connected to the interior volume to receive a flow of toxins therefrom,
       wherein the inlet is fluidly connected to a first chamber in the enclosure and the outlet is fluidly connected to a second chamber in the enclosure, the first and second chambers separated by the annular hemofilter.

2. The artificial kidney of claim 1, wherein both the first chamber and the second chamber have a tapering height from the central axis to a periphery of the enclosure.

3. The artificial kidney of claim 2, wherein the first chamber and the second chamber are symmetrical to each other.

4. The artificial kidney of claim 1, wherein the enclosure is radially symmetrical about the central axis.

5. The artificial kidney of claim 1 further comprising a second inlet proximate the central axis fluidly connected to the interior volume to receive a flow of dialysate therein.

6. The artificial kidney of claim 5, wherein the second outlet is proximate the central axis and fluidly connected to the second inlet.

7. The artificial kidney of claim 1 comprising a plurality of annular hemofilter pairs connected in series.

8. The artificial kidney of claim 1 comprising a plurality of annular hemofilter pairs connected in parallel.

9. An artificial kidney comprising:
   an annular hemofilter having a circular or oval shape, the annular hemofilter having an inner diameter and an outer diameter; and
   an enclosure having a shape corresponding to the hemofilter, the enclosure having a thickness, a diameter, and an interior volume for receiving and enclosing the hemofilter therein, with the enclosure thickness less than the enclosure diameter, the enclosure having a blood inlet, and a blood outlet proximate a central axis;
   the artificial kidney having a radial blood flow path across the annular hemofilter from the inner diameter to the outer diameter.

10. The artificial kidney of claim 9 further comprising a blood inlet centrally located in the enclosure and fluidly connected to the interior volume.

11. The artificial kidney of claim 10 further comprising a dialysate inlet centrally located in the enclosure and fluidly connected to the interior volume.

12. The artificial kidney of claim 10 wherein the blood inlet is fluidly connected to a first chamber in the enclosure and a blood outlet is fluidly connected to a second chamber in the enclosure, the first and second chambers separated by the annular hemofilter.

13. The artificial kidney of claim 12, wherein both the first chamber and the second chamber have a tapering height from the inner diameter to the outer diameter.

14. The artificial kidney of claim 12 comprising a plurality of annular hemofilter pairs connected in series.

15. The artificial kidney of claim 12 comprising a plurality of annular hemofilter pairs connected in parallel.

* * * * *